United States Patent
Cremer

[11] Patent Number: 5,853,760
[45] Date of Patent: Dec. 29, 1998

[54] DEVICE FOR THE CONTROLLED RELEASE OF ACTIVE SUBSTANCES

[75] Inventor: Karsten Cremer, Bonn, Germany

[73] Assignee: LTS Lohmann Therapie-Systeme GmbH & Co. KG, Neuwied, Germany

[21] Appl. No.: 348,493

[22] Filed: Dec. 2, 1994

[30] Foreign Application Priority Data

Dec. 4, 1993 [DE] Germany ............................ 43 41 442.7

[51] Int. Cl.⁶ ............................. A61K 9/24; A61K 9/28
[52] U.S. Cl. ..................... 424/484; 424/474; 514/964; 71/64.13
[58] Field of Search ...................... 424/484, 472, 424/474, 476–477, 479–482, 426, 428, 408; 21/64.13, 904

[56] References Cited

U.S. PATENT DOCUMENTS

| | | | |
|---|---|---|---|
| 2,798,024 | 7/1957 | Zapapas et al. | 424/471 |
| 3,383,283 | 5/1968 | Brindamour | 424/476 |
| 3,625,214 | 12/1971 | Higuchi | 424/426 |
| 4,814,182 | 3/1989 | Graham et al. | 424/484 |
| 5,284,659 | 2/1994 | Cherukuri | 424/471 |
| 5,391,378 | 2/1995 | Sanderson | 424/474 |
| 5,422,123 | 6/1995 | Conte et al. | 424/479 |
| 5,601,843 | 2/1997 | Gimet et al. | 424/474 |

FOREIGN PATENT DOCUMENTS

| | | |
|---|---|---|
| 127282 | 3/1984 | European Pat. Off. . |
| 259219 | 3/1988 | European Pat. Off. . |
| 432607 | 6/1991 | European Pat. Off. . |
| 542364 | 11/1992 | European Pat. Off. . |
| 2448631 | 4/1975 | Germany . |
| 3809978 | 10/1989 | Germany . |

OTHER PUBLICATIONS

Theeuwes, Pharm. Int. 5, p. 293, 1984.
Higuchi, J. Pharm. Sci. 50, p. 874, 1961.

*Primary Examiner*—Edward J. Webman

[57] ABSTRACT

A device for the controlled release of active substances in liquid media from an active substance-containing matrix exhibiting active substance releasing-surfaces has, the active substance releasing surfaces of the matrix covered, at least partially, by an erodible mass of solids; the thickness of the erodible mass across its extent on the active substance releasing-areas is determined by gradients.

14 Claims, 2 Drawing Sheets

DEVICE FOR THE CONTROLLED RELEASE OF ACTIVE SUBSTANCES

BACKGROUND OF THE INVENTION

1. Field of the Invention

The present invention relates to a device for the controlled release of active substances in liquid media from an active substance-containing matrix having active substance-releasing areas and an erodible mass of solids which covers the active substance-releasing areas at least partially.

The device makes it possible to release active substances with a given velocity profile in liquid media, e.g., body fluids, such as hydrochloric acid, in order to achieve certain plasma levels over an extended period of time. In this connection, active substances, e.g., after peroral application, can be released to the gastric and intestinal juice at a controlled rate. After application by means of implantation, the interstitial tissue fluid constitutes the medium through which the device, being in direct contact therewith, releases the active substances.

Another field of application is the specific release of active substances which provide plant protection and/or plant growth to liquids which are absorbed by plants. This may be effected, for instance, by introducing devices according to the present invention into vessels or ducts containing sprinkling or irrigation liquid. Also, the direct application into the ground is possible within the scope of the present invention since, in general, there is sufficient capillary water to allow erosion of the erodible mass and thus release of the active substance. Another possible application results from the controlled release of antibacterial active substances, in particular in flushing and washing facilities for the domestic or clinical use.

Devices having a controlled active substance release are frequently used to administer active substances having a short biological half-life, e.g., in case of pharmaceutical peroral agents, in a manner which, connected with a low frequency of taking, avoids noticeable variations of the plasma concentrations. Usually, this aim is achieved by devices releasing active substances over an extended period of time at a constant rate. Sometimes, however, changing the release rate also results in relatively constant plasma levels, for instance, when an active substance is absorbed in different sections of the gastro-intestinal tract at very different rates.

The advantage of slight concentration variations in the plasma lie in both avoidance of toxic effects, which may result from the high maximum concentrations after taking conventional peroral agents, and a prolongation of the therapeutic action. In addition, a reduced taking frequency promotes the reliability of the patients with respect to regular taking.

2. The Prior Art

It has been known for some time that a controlled active substance release can sometimes be achieved by physico-chemical measures to which an active substance is subjected. These measures include the use of adsorbates, slightly soluble salts or complexes. However, a more effective control over the degree of retardation is generally achieved by galenic measures. Most of the known devices for the controlled release of active substances can be classified into two types, i.e., the matrix systems and the membrane systems. Matrix systems comprise the active substance in dissolved or dispersed form, in rare cases in the form of multiparticulate pharmaceutical intermediates. The release is either effected by diffusion of active substances from the matrix or by erosion of the matrix. In contrast to this, membrane systems consist of an active substance-containing reservoir which is enclosed by a polymer film permeable to the active substance. In this case, the release is effected by diffusion through the matrix.

The release rate depends on different factors. In the case of matrix systems these include, among other things, specific properties of the substances used, e.g., molecular mass, solubility, swelling capacity, and glass transition temperature, but also the active substance concentration and the geometric form of the matrix. When the release takes place by diffusion, the main factors include the size of the surface, the matrix volume, the diffusion coefficient, the concentration and solubility of an active substance in the matrix, the porosity and tortuosity of the matrix, and the diffusion resistance between matrix and a liquid ambient medium. Membrane systems release active substances at a rate which mainly depends on the size of the surface, the permeability of the active substance in the membrane, and the concentration gradient to both sides of the membrane.

Matrix and membrane systems which influence rate by their specific geometric shape have already been known. These are devices in which an erosion front which migrates in the course of the release changes its dimension. Examples thereof include devices whose erosion surface enlarges in order to maintain a constant release rate (Brooke, DE-0 24 48 631; McMullen, Eur. Pat. Appl. 0 259 219; Chopra et al., Eur. Pat. Appl. 0 542 364). To achieve the contrary effect, i.e., the controlled reduction of the release rate, a reservoir has been described the erosion front of which becomes smaller in the course of release (Hermann, DE 38 09 978).

Additionally, devices are known achieving a control of the release rate by the fact that they contain one or more layers which are free from active substance and substantially impermeable and which cover a part of their surface (Zaffaroni, Eur. Pat. Appl. 0 127 282; Graham et al., U.S. Pat. No. 4,814,182; Conte et al., Eur. Pat. Appl. 0,432,607).

As an alternative to the widespread matrix and membrane systems special devices for the controlled release of active substances have been developed, which comprise an active substance reservoir in which an osmotic pressure builds up after the entry of water. The membranes surrounding the active substance reservoir are semipermeable, i.e., they allow entry of water but are impermeable to active substances, however, have a microscopic opening through which both diffused water and dissolved active substance can flow out. One advantage of such osmotically active devices is the fact that they can achieve very constant release rates over extended periods of time (Theeuwes, Pharm.Int. 5, p. 293, 1984).

The realization of controlled release rates using conventional matrix or membrane systems frequently involves difficulties. In case of erodible matrices the release rate—depending on the shape of the matrix—slows down in the course of the release to a more or less considerable extent due to the size reduction of the erodible surface. The above-mentioned devices which compensate a deceleration by the special geometric shaping of the matrix are difficult to realize from the technical point of view. In diffusion matrices, however, a continuously growing diffusion layer forms owing to the increasing active substance depletion; as a consequence the release rate reduces as a function of $t^{1/2}$ (Higuchi, J. Pharm. Sci. 50, p. 874, 1961).

Theoretically, membrane systems can have a constant release rate as long as the reservoir comprises the active substance at its saturation concentration in dissolved form. This is the case when, in addition to the dissolved active substance, undissolved active substance which dissolves in the reservoir quickly enough to substitute the already released active substance is present in the device. As soon as the concentration falls below the saturation concentration, the release slows down in proportion to the decline of the concentration gradient to both sides of the membrane.

The above-mentioned osmotically controlled systems release active substances at a constant rate, however, their production requires the use of a particularly expensive technology. Another drawback of these devices is the risk of gastro-intestinal mucous membrane damages after peroral application. Finally, they are relatively unsuitable in all cases where a release profile is desired that is different from a constant rate.

SUMMARY OF THE INVENTION

It is an object of the present invention to provide a device releasing active substances at a controlled rate into a liquid medium, however, while avoiding of the above-mentioned drawbacks of the prior art.

The above object is achieved according to the present invention by a device for the controlled release of active substances in liquid media comprising an active substance-containing matrix having active substance releasing areas, said active substance releasing areas comprising surfaces of said matrix which are covered, at least partially, by an erodible mass of solids; and said erodible mass having a thickness which extends on the active substance releasing areas surfaces and is determined by gradients.

The present invention includes the selective use of thickness gradients so that an erodible mass is eroded at the intended rate and thus effects an enlargement of the contact surface of the active substance-containing matrix to the ambient liquid.

The term "erosion" has generally been adopted in the pharmaceutical technology for all processes in which solid masses are "cleared away". In this connection, it is not decisive whether the mass reduction of a solid body takes place by the fact that solid components go into solution and consequently diffuse off, or whether a chemical decomposition takes place first in which, for example, long polymer chains are cleaved into more readily soluble oligomers, monomers, or other degradation products.

In a device according to the present invention not more than a part of the matrix surface is in contact with the liquid outer medium in the beginning of the active substance release, and thus available as release surface. In the further course of the release, the active substance concentration in the matrix reduces. However, this effect does not result in a reduction of the release ratep—as is the case in conventional matrix systems—since the erosion of the erodible layer which is in contact with the matrix proceeds at the same time, resulting in a continuous enlargement of the release area of the matrix. Therefore, the increase of the release surface in the course of time is of decisive importance with respect to the control of the release rate. For instance, a release according to zero order is obtained when the increase of the release area exactly compensates the effect of the decreasing active substance concentration.

The solution according to the present invention is of particular advantage with respect to its simplicity and flexibility. Erodible masses having thickness gradients controlling the erosion rate can be manufactured by any common pharmaceutic-technological production technique. Active substance-containing matrices of different formulation types may be turned into devices having a controlled active substance release by means of applying an erodible mass according to the present invention. The frequently desired release at a constant rate—but also other release profiles— can be realized very exactly. Deviations from the desired release profile may be corrected by modifying the shape of the erodible mass even after decision on a certain formulation.

When the device is used as a drug, the erodible mass generally includes physiologically acceptable polymers or waxy substances and, optionally, further pharmaceutical adjuvants. Examples of these polymers include polysaccharides, such as gums, starch derivatives or cellulose derivatives, polyacrylates and polymethacrylates, polylactides, polyglycolides, polyoxyethylenes, and polyoxypropylenes, proteins, polyvinyl alcohol, polyvinyl acetate, polyvinyl chloride or polyvinyl pyrolidone. Waxy substances, for example, are hydrogenated castor oil or cetostearyl alcohol. Additional pharmaceutical adjuvants may come from the groups consisting of stabilizers, solubilizers, surfactants, fillers, softeners, hydrophilizing agents, pigments and dyes, substances for the adjustment of the pH-value, flow regulators, release agents, lubricants, and the like. Depending on the compatibility and desired erosion rate, the portion of the individual components may be adjusted.

When used in plant protection and similar fields, the biocompatability—in contrast to the biodegradability—does not play an important role.

A preferred embodiment for producing a device according to the present invention is to manufacture the active substance-containing matrix itself as a layer structure and then to coat it, at least partially, with at least one erodible layer.

BRIEF DESCRIPTION OF THE DRAWINGS

Other objects and features of the present invention will become apparent from the following detailed description considered in connection with the accompanying drawing which discloses several embodiments of the present invention. It should be understood, however, that the drawing is designed for the purpose of illustration only and not as a definition of the limits of the invention.

In the drawing, wherein similar reference characters denote similar elements throughout the several views:

FIG. 1 shows devices according to the present invention with a layered structure of the active substance-containing matrix;

FIG. 1b shows another embodiment similar to FIG. 1a;

FIG. 1c shows a further embodiment similar to FIG. 1a;

FIG. 2 shows other devices according to the present invention with matrices having an uneven surface, and the resulting recesses in the matrix surface are filled by the erodible layer;

DETAILED DESCRIPTION OF PREFERRED EMBODIMENTS

Turning now in detail to the drawings, FIG. 1 shows devices according to the present invention with a layered structure of the active substance-containing matrix 1. The active substance-containing matrix may either have one erodible layer, as shown in FIGS. 1a to 1c, or several ones, as shown in FIGS. 1d to 1e. In some cases it will be sufficient to form the erodible layer(s) in a wedge-shaped manner 2, as shown in FIGS. 1a, 1d, and 1e, to control the release rate; in other cases it will be preferable to form the erodible layers 3 as spherical segments, as shown in FIGS. 1b and 1f. In order to control the release rate exactly and be able to adapt it to each desired course and each matrix type, it is also possible to use at least one erodible layer having thickness gradients varying across its extent according to complex contours or functions 4, as shown in FIG. 1c.

Figure 1A:
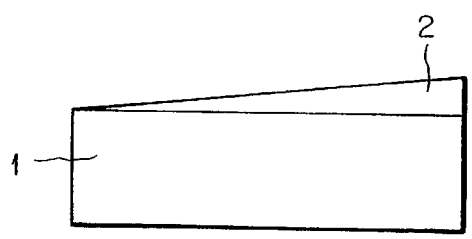
FIG. 1a shows an embodiment of the device in which the active substance-containing matrix has one erodible layer.
Figure 1B:
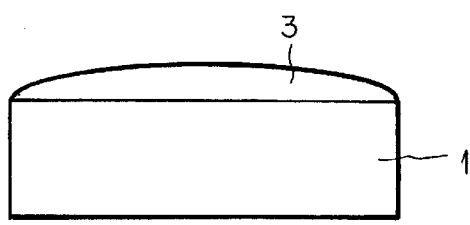
Figure 1C:
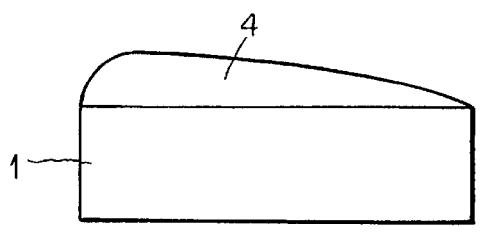
Figure 1D:
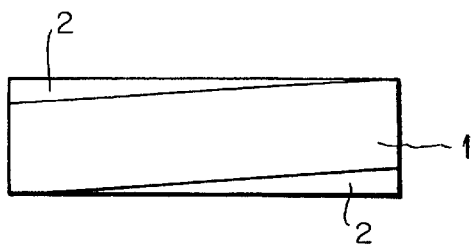
FIG. 1d shows an embodiment of the device in which the active substance-containing matrix has several erodible layers.
Figure 1E:
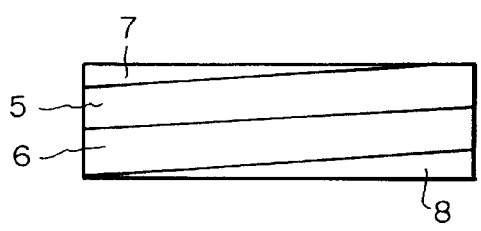
FIG. 1e shows another embodiment similar to FIG. 1d.
Figure 1F:
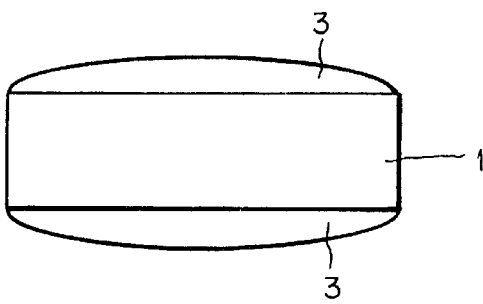
FIG. 1f shows a further embodiment similar to FIG. 1d.
Figure 2A:
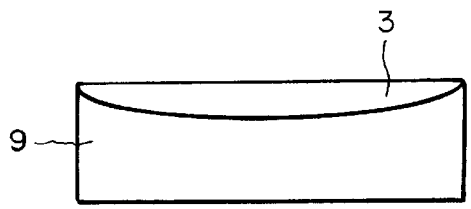
FIG. 2a shows an embodiment having an uneven surface and one erodible layer with a spherical segment.
Figure 2B:
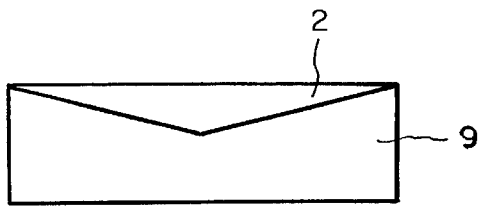
FIG. 2b shows an embodiment having an uneven matrix and one wedge-shaped erodible layer.
Figure 2C:
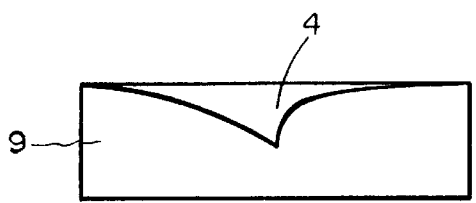
FIG. 2c shows an embodiment having an uneven matrix with an erodible layer exhibiting thickness gradient.
Figure 2D:
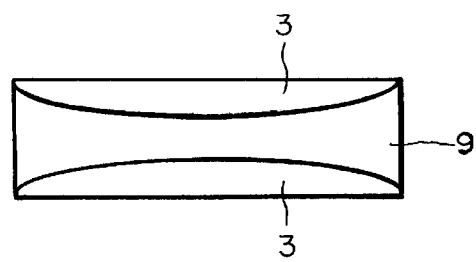
FIG. 2d shows an embodiment having an uneven surface and several erodible layers.
Figure 2E:
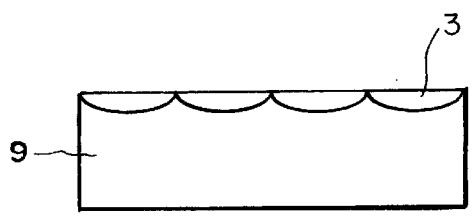
FIG. 2e shows a further embodiment similar to FIG. 2d.
Figure 2F:
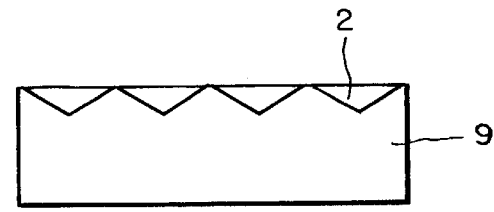
FIG. 2f shows an embodiment having an uneven matrix and several wedge-shaped erodible layers.

In another embodiment, it is possible that the active substance-containing matrix has a multi-layer structure. This is the case, for instance, when the device comprises more than one active substance and differently formed erodible layers are necessary to achieve the desired release profile. FIG. 1e shows a device having a double-layer active substance-containing matrix comprising the two subunits 5 and 6 having an erodible layer 7 which controls the active substance release from the matrix subunit 5 and another erodible layer 8 which controls the release profile from the second subunit 6 of the matrix.

It may be favorable from the process technological point of view to apply the erodible layer(s) on active substance-containing matrices whose forms have been modified.

FIG. 2 shows devices according to the present invention comprising matrices having an uneven surface 9; the resulting recesses in the matrix surface are filled by the erodible layers. FIG. 2a shows a device according to the present invention having an uneven surface 9 and one erodible layer 3 having the form of a spherical segment; in FIGS. 2d and 2e the matrix has several of these layers. FIGS. 2b and 2f show devices having an uneven matrix 9 and one or more wedge-shaped erodible layers 2. FIG. 2c shows the combination of an uneven matrix with an erodible layer exhibiting thickness gradients which vary across the extension of the layer according to complex contours or functions 4. In all examples shown in FIG. 2 the erodible layers adapt to the contours of the matrix surface. For this reason, the outer shape of the devices can be regular, irrespective of the form of the erodible layer and of the matrix.

Figure 3:
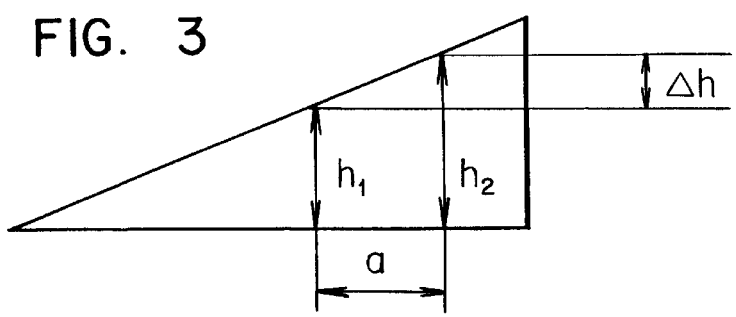
FIG. 3 shows the thickness gradient of the device of the invention.

According to the present invention a "thickness gradient" is to be understood as a geometric shaping of the mass (FIG. 3), by which the erodible mass has a different thickness "h" in various places. The change in the thickness over a unit of length "a" of the erodible mass, i.e., $\Delta h/\Delta a$, is a thickness gradient. An erodible mass according to the present invention may have one single thickness gradient (cf. FIG. 1a); in this case $\Delta h/\Delta a$ remains constant. If $\Delta h/\Delta a$ varies continuously over the distance "a" (cf. FIG. 1b), there is a different thickness gradient for each place.

Active substance-containing matrices which are suitable as component of the devices according to the present invention may be manufactured by many common pharmaceutical manufacturing technologies. For instance, matrices having a layered structure may be manufactured by compressing powders, powder mixtures or granular powders by means of conventional tableting tools. Also, multi-layer matrices may be produced by compressing. Thin matrices, for example, may be produced by means of casting or coating methods wherein solutions or suspensions are applied as a thin layer on a generally intermediate substrate and dried. Additionally, processes using melts are suitable for the production of the matrices. These include, e.g., injection molding and extrusion.

According to the present invention, the erodible layers may be manufactured by the same processes as those available for the production of the active substance-containing matrices. In this connection, it is not important whether active substance-containing matrix and erodible layer are manufactured one after the other or at the same time. If the adhesion between matrix and erodible layer is insufficient, it may be necessary to use adhesion promoters. These are physiologically acceptable polymers having adhesive properties which continue to exist even in the presence of water. It is also possible that the erodible mass is an active substance-containing mass.

Among other things, devices according to the present invention may be used to administer, by controlled release, pharmaceutical active substances for therapeutic or diagnostic purposes and to achieve constant plasma levels. Another possibility of application is the selective release of active substances which promote plant protection or plant growth in liquids, such as fertilizer active substances which are absorbed by plants; or for the release of antibacterial substances for washing accommodations and/or flushing installations in domestic, industrial (bottle washing machines) or clinical sectors.

While only several embodiments of the present invention have been shown and described, it is to be understood that many changes and modifications may be made thereunto without departing from the spirit and scope of the invention as defined in the appended claims.

What is claimed is:

1. A device for the controlled release of at least one active substance into a liquid medium comprising a controlled release active substance-containing matrix, said matrix having an active substance releasing surface, and at least one covering layer containing a solid material which is erodible in said liquid medium, said covering layer covering at least partially said active substance releasing surface of said matrix, wherein said covering layer has a thickness profile with at least one thickness gradient different from zero and wherein the erosion of said covering layer having said thickness profile effects a controlled and continuous uncovering of said partially covered active substance releasing surface.

2. A device according to claim 1, wherein said active substance-containing matrix comprises at least one active substance containing layer.

3. A device according to claim 1, further comprising an adhesive means between said active substance-containing matrix and said covering layer.

4. A device according to claim 1, wherein said thickness gradient is a constant different from zero.

5. A device according to claim 1, wherein said thickness gradient is a continuous function over the distance of said at least partially covered surface of said matrix different from zero.

6. A device according to claim 1, wherein said covering layer is wedge-shaped.

7. A device according to claim 1, wherein said covering layer has the form of a spherical segment.

8. A device according to claim 1, wherein said covering layer completely covers at least one side of the active substance releasing surface.

9. A device according to claim 1, wherein said covering layer further comprises at least one active substance.

10. A method for the controlled administration of an active substance comprising a drug to a patient, which method comprises administering to said patient a device for the controlled release of said active substance drug into a liquid medium and said device comprising a controlled release active substance-containing matrix, said matrix having an active substance releasing surface, and at least one covering layer containing a solid material which is erodible in said liquid medium, said covering layer covering at least partially said active substance releasing surface of said matrix, wherein said covering layer has a thickness profile with at least one thickness gradient different from zero and wherein the erosion of said covering layer having said thickness profile effects a controlled and continuous uncovering of said partially covered active substance releasing surface.

11. A method for the controlled delivery of an active substance to a plant which comprises incorporating into a liquid medium to be applied to said plant or to the locus of said plant, wherein said active substance is an agent for plant protection, a device for the controlled release of said active substance into said liquid medium comprising a controlled release active substance-containing matrix, said matrix having an active substance releasing surface, and at least one covering layer containing a solid material which is erodible in said liquid medium, said covering layer covering at least partially said active substance releasing surface of said matrix, wherein said covering layer has a thickness profile with at least one thickness gradient different from zero and wherein the erosion of said covering layer having said thickness profile effects a controlled and continuous uncovering of said partially covered active substance releasing surface; and applying said liquid medium to said plant or to the locus of said plant, is a fertilizer, and subsequently applying said liquid to said plant or to the locus of said plant.

12. A method for the controlled delivery of an active substance to a plant which comprises incorporating into a liquid medium to be applied to said plant or to the locus of said plant a device of claim 1, wherein said active substance is a fertilizer, and subsequently applying said liquid to said plant or to the locus of said plant.

13. A method for the controlled delivery of an active substance into water which comprises introducing a device of claim 1, into said water wherein said active substance is an antibacterial agent.

14. A device of claim 1, wherein said active substance-containing matrix is a tablet.

* * * * *